(12) United States Patent
Schneidinger et al.

(10) Patent No.: US 6,905,689 B2
(45) Date of Patent: Jun. 14, 2005

(54) CONJUGATE OF A TISSUE NON-SPECIFIC ALKALINE PHOSPHATASE AND DEXTRAN, PROCESS FOR ITS PRODUCTION AND USE THEREOF

(75) Inventors: Bernd Schneidinger, Hohenschaeftlarn/Neufahrn (DE); Thomas Meier, Munich (DE); Rainer Schmuck, Benediktbeuern (DE); Zhixin Shao, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 141 days.

(21) Appl. No.: 10/624,154

(22) Filed: Jul. 21, 2003

(65) Prior Publication Data

US 2004/0082027 A1 Apr. 29, 2004

(30) Foreign Application Priority Data

Jul. 22, 2002 (EP) .............................................. 02016244

(51) Int. Cl.$^7$ ......................... A61K 39/385; C12Q 1/42; C12N 9/16; C07H 21/04; C07K 14/00
(52) U.S. Cl. ...................... 424/193.1; 435/21; 435/196; 536/23.2; 530/350
(58) Field of Search ......................... 424/193.1; 435/21, 435/196; 536/23.2; 530/350

(56) References Cited

U.S. PATENT DOCUMENTS

| | | | |
|---|---|---|---|
| 4,931,392 A | 6/1990 | Rehner et al. | 435/188 |
| 4,950,609 A | 8/1990 | Tischer et al. | 435/18 |
| 5,434,067 A | 7/1995 | Michaelis et al. | 435/196 |
| 5,514,559 A | 5/1996 | Markert-Hahn et al. | 435/7.92 |
| 5,834,273 A | 11/1998 | Rutasugi et al. | 435/177 |

FOREIGN PATENT DOCUMENTS

| | | |
|---|---|---|
| EP | 0 418 523 | 3/1991 |
| EP | 0 471 125 | 2/1992 |
| WO | WO 93/01498 | 1/1993 |

OTHER PUBLICATIONS

Anderson, et al., (1991), Int. J. Cancer, "Binding of epidermal growth factor–dextran conjugates to cultured glioma cells", vol.: 47, pp. 439–444.
Balbas, P., (2001), Molecular Biotechnology, "Understanding the art of producing protein and nonprotein molecules in *escherichia coli*", vol.: 19, pp. 251–267.
Bretaudiere and Spillman, (1984), Verlag Chemie, "Methods of enzymatic analysis", vol.: IV, Third Edition, pp. 75–83.
Bradford, M.M., (1976), Analytical Biochemistry, "A rapid and sensitive method for the quantitation of microgram quantities of protein utilizing the principle of protein–dye binding", vol.: 72, pp. 248–254.

Fukushi, M., et al., (1998), Biochemical and Biophysical Research Communications, "Intracellular retention and degradation of tissue–nonspecific alkaline phosphatase with a Gly$^{317 \rightarrow}$ Asp substitution associated with lethal hypophosphatasia", vol.: 246, pp. 613–618.
Harris, H., (1989), Clinica Chimica Acta, "The juman alkaline phosphatases: What we know and shat we don't know", vol.: 186, pp. 133–150.
Holmberg, A., et al., (1993), Bioconjugate Chem., "Preparation of sulfhydrylborane–dextran conjugates for boron neutron capture therapy", vol.: 4, pp. 570–573.
Hooper, N.M, (1997), Clinica Chimica Acta, "Glycosyl–phosphatidylinositol anchored membrane enzymes", vol.: 266, pp. 3–12.
Lilie, H., et al., (1998), Curr. Opin. Biotechnol., "Advances in refolding of proteins produced in *E. coli*", vol.: 9, pp. 497–501.
Lovqvist, A., et al., (1993), Cancer Biotherapy, "Binding, internalization and excretion of TGF $_\alpha$–dextran associated radioactivity in cultured human glioma cells", vol.: 8(4), pp. 345–356.
Makrides, S.C., (1996), Microbiological Reviews, "Strategies for achieving highj–level expression of genes in *Escherichia coli*", vol.: 60(3), pp. 512–538.
Maldonado, O., et al., (1998), J. Clin Gastroenterol, "Extremely high levels of alkaline phosphatase in hospitalized patients", vol.: 27(4), pp. 342–345.
Miura, M., et al., (1994), Ann Clin Biochem, "Differences between the sugar moieties of liver– and bone–type alkaline phosphatases: a re–evaluation", vol.: 31, pp. 25–30.
Moss, D.W., (1992), Clin. Chem., "Perspectives in alkaline phosphatase research", vol.: 38(12), pp. 2486–2492.
Mulivor, R.A., et al., (1985), J. Lab. Clin. Med., "Quantitative analysis of alkaline phoshatases in serum and amniotic fluid: Comparison of biochemical and immunologic assays", vol.: 105(3), pp. 342.348.
Nosjean, O., et al., (1997), Biochem. J., "Human tissue non–specific alkaline phosphatases: sugar–moiety–induced enzymic and antigenic modulations and genetic aspects", vol.: 321, pp. 297–303.
Oda, K., et al., (1999), J. Biochem., "A general method for rapid purification of soluble versions of glycosylphosphatidylinositol–anchored proteins expressed in insect cells: An application for human tissue–nonspecific alkaline phosphatase", vol.: 126, pp. 694–699.

(Continued)

Primary Examiner—Tekchand Saidha
(74) Attorney, Agent, or Firm—McDonnell Boehnen Hulbert & Berghoff LLP

(57) ABSTRACT

A conjugate of a tissue non-specific alkaline phosphatase (tns-AP) and dextran which can be obtained by reacting unglycosylated tns-AP with activated dextran by incubation in aqueous solution, stopping the reaction and isolating the conjugate from the solution. The conjugate obtained in this manner is suitable as a standard for the determination of alkaline phosphatase.

9 Claims, 6 Drawing Sheets

OTHER PUBLICATIONS

Olsson, P., et al., (1994), Int. J. Cancer., "Internalization and excretion of epidermal growth factor–dextran–associated radioactivity in cultured human squamous–carcinoma cells", vol. 56, pp. 529–537.

Reddy, S., et al., (1995), Biochemistry, "$N^\Sigma$–(Carboxymethyl) lysine is a dominant advanced glycation end product (AGE) antigen in tissue proteins", vol.: 34, pp. 10872–10878.

Romagnoli, E., et al., (1998), Clin. Chem. Lab. Med., "Assessment of serum total and bone alkaline phosphatase measurement in clinical practice", vol.: 36(3), pp. 163–168.

Silve, C., (1994), Current Opinion in Rheumatology., "Hereditary hypophosphatasia and hyperphosphatasia", vol.: 6, pp. 336–339.

Singh, R., et al., (2001), Diabetologia, "Advanced glycation end–products: a review", vol.: 44, pp. 129–146.

Sjostrom, A., et al., (1997), Int. J. Cancer., "Binding, internalization and degradation of EGF–Dextran conjugates in two human bladder–cancer cell lines", vol.: 70, pp. 383–389.

Thornalley, P.J., et al., (1999), Biochem. J., "Formation of glyoxal, methylglyoxal and 3–deoxyglucosone in the glycation of proteins by glucose", vol.: 344, pp. 109–116.

Tietz, N.W., et al., (1983), J. Clin. Chem. Clin. Biochem., "IFCC methods for the measurement of catalytic concentration of enzymes", vol.: 21(11), pp. 731–748.

Weiss, M.J., et al., (1988), The Journal of Biological Chemistry, "Strujcture of the human liver/bone/kidney alkaline phosphatase gene", vol.: 263(24), pp. 12002–12010.

Weiss, M.M., et al., (1986), Proc. Natl. Acad. Sci. USA, "Isolation and characterization of a cDNA encoding a human liver/bone/kidney–type alkaline phosphatase", vol.: 83, pp. 7182–7186.

Wiwanitkit, V., (2001), BMC Family Practice 2001, "High serum alkaline phosphatase levels, a study in 181 Thai adult hospitalized patients", vol.: 2(2), 4 page article.

PCR htns_AP (1637 bps)

pelB-AP_N (501 bps)

CONJUGATE OF A TISSUE NON-SPECIFIC ALKALINE PHOSPHATASE AND DEXTRAN, PROCESS FOR ITS PRODUCTION AND USE THEREOF

The invention concerns a conjugate of a tissue non-specific alkaline phosphatase and dextran, a process for the production of such a conjugate and its use.

Alkaline phosphatases (AP, EC 3.1.3.1) belong to a ubiquitous family of dimeric metalloenzymes which catalyse the hydrolysis of phosphomonoesters under alkaline conditions with release of inorganic phosphate (McComb et al., (1979), Alkaline Phosphatases, Plenum Press, New York). One can distinguish between four isoenzymes in humans: i) placenta-specific AP, ii) germ cell specific (placental) AP, iii) intestinal AP and iv) the tissue non-specific AP (tns-AP) (Harris, H., Clin. Chim. Acta 186 (1990) 133–150). The production of tns-AP is strongest in the liver (LAP), kidney (KAP) and bones (BAP) (Moss, D. W., Clin. Chem. 38 (1992) 2486–2492) and is the most frequent AP isoform in serum (Mulivor, R. A., et al., J. Lab. Clin. Med. 105 (1985) 342–348). The differences between LAP, KAP and BAP are due to different posttranslational O-glycosylation patterns (Miura, M., et al., Ann. Clin. Biochem. 31 (1994) 25–30) which also results in different specific activities (Nosjean, O., et al., Biochem. J. 321 (1997) 297–303) although their amino acid sequences are essentially identical (Weiss, M. J., et al., J. Biol. Chem. 263 (1988) 12002–12010). Furthermore Nosjean et al. have shown that the N-glycosylation of tns-AP is essential for its enzymatic activity. Consequently tissue non-specific AP is a mixture of different glycosylated APs.

The gene for human tns-AP was already cloned in 1986 (Weiss, M. J., et al., Proc. Natl. Acad. Sci. USA 84 (1986) 7182–7186). It codes for a protein consisting of 524 amino acids with a 17 amino acid long N-terminal signal sequence and a C-terminal GPI anchor sequence with which the protein is anchored in vivo to the outside of the plasma membrane (Hooper, N. M., Clin. Chim. Acta 266 (1997) 3–12). Although the DNA sequence of human tns-AP has been known for a long time, only the expression of a recombinant, biologically active enzyme in eukaryotic cells such as COS-1 (Fukushi, M., et al., Biochem. Biophys. Res. Commun. 246 (1998) 613–618) or insect cells infected with baculovirus (Oda, K., et al., J. Biochem. (Tokyo) 126 (1999) 694–699) has been previously reported.

The heterologous expression of proteins in prokaryotes such as *Escherichia coli* is a technology that is frequently used for the safe and cost-effective production of recombinant proteins. The expression of eukaryotic proteins in prokaroytes has two characteristics: i) prokaryotes such as *E. coli* do not carry out a number of post-translational modifications such as glycosylations that are typical for eukaroytes and ii) eukaryotic proteins expressed in prokaryotes are often present in the form of poorly soluble, biologically inactive protein aggregates (inclusion bodies, IBs) (Makrides, S. C., Microbiol. Rev. 60 (1996) 512–538; Balbas, P., Mol. Biotechnol. 19 (2001) 251–267). The latter can be converted back into an enzymatically active form by known methods (Lilie, H., et al., Curr. Opin. Biotechnol. 9 (1998) 497–501). For this purpose the IBs are firstly dissolved by adding a chaotropic agent such as urea and renatured by dialysis or dilution in a chaotrope-free buffer. A method for renaturing a placenta-specific alkaline phosphatase is described in the prior art (U.S. Pat. No. 5,434,067).

Although the physiological role of alkaline phosphatase is largely unknown, the determination of its enzymatic activity is one of the routine analyses in clinical diagnostics. A change in the AP activity in serum is a diagnostic marker for a large number of clinical conditions such as hypophosphatasia and hyperphosphatasia (Silve, C., Curr. Opin. Rheumatol. 6 (1994) 336–339), diseases of the liver, the bile ducts and sepsis (Maldonado, O., et al., J. Clin. Gastroenterol. 27 (1998) 342–345; Wiwanitkit, V., BMC Fam. Pract. 2 (2001) 2) and also bone diseases (Romagnoli, E., et al., Clin. Chem. Lab. Med. 36 (1998) 163–168). The serum contains a heterogeneous mixture of various forms of AP. As already stated above, the ratio of LAP, KAP and BAP which together form tns-AP also varies from patient to patient since the ratio of the individual forms of AP in serum is dependent on the type and severity of the individual disease of the patient.

For this reason it is difficult to provide suitable reference and standard samples. Serum pools consisting of sera from patients with normal AP values and increased AP values are usually used; but preparations of normal LAP or BAP are also used. The reference samples used for the determination of alkaline phosphatase in human serum or plasma are also derived from animal sources such as cows or pigs, from human cell lines or human placenta. This is associated with various disadvantages: The isolation of enzymes from animal or human tissue is associated with a high risk of infection (HIV, BSE) and is technically very complicated. Due to the lack of alternatives the International Federation of Clinical Chemistry and Laboratory Medicine (IFCC) presently recommends the use of a tns-AP isolated from porcine kidneys as a reference enzyme (Tietz, N. W., et al., J. Clin. Chem. Clin. Biochem. 21 (1983) 731–748).

The object of the present invention is to provide a preparation of an AP which can be used as a reference in clinical diagnostics and can be produced reproducibly and in a simple manner.

The invention concerns a conjugate of a tissue non-specific alkaline phosphate (tns-AP) and dextran obtainable by reacting unglycosylated tns-AP with activated dextran in aqueous solution, stopping the reaction and isolating the conjugate from the solution.

It was surprisingly found that a conjugate according to the invention is enzymatically active, has the properties of a tns-AP and is therefore particularly suitable as a standard in AP tests. Moreover, the measured AP activity of the conjugate according to the invention in the reagent which is recommended by the IFCC (Tietz et al., supra) does not significantly depend on the buffer concentration.

| IFCC reagent and reaction conditions: | |
|---|---|
| Temperature | 30 ± 0.05° C. |
| pH (30° C.) | 10.40 ± 0.05 |
| 2-amino-2-methyl-1-propanol buffer | 0.35 mol · $1^{-1}$ |
| 4-nitrophenyl phosphate | 10.0 mmol · $1^{-1}$ |
| magnesium acetate | 2.0 mmol · $1^{-1}$ |
| zinc sulphate | 1.0 mmol · $1^{-1}$ |
| N-hydroxyethylethylenediaminetriacetic acid (HEDTA) | 2.0 mmol · $1^{-1}$ |
| volume fraction of the sample | 0.0196 (1:51) |

Surprisingly the same activities for the standard according to the invention were measured in a buffer range of 0.35–0.90 mol/l in the IFCC test. With respect to other properties the standard according to the invention behaves like a control serum in the IFCC test. In constrast, comparative experiments show that a conjugate of unglycosylated tns-AP and glucose (glucosylated tns-AP) is unsuitable as a standard.

A tissue non-specific alkaline phosphatase (tns-AP) is understood according to the invention as an alkaline phosphatase which can be isolated in a glycosylated form from human liver, bones or kidney (EC 3.1.3.1). The nucleotide sequence of tns-AP is described by Weiss et al., 1986 supra. According to Nosjean et al., supra tns-APs from liver, bone and kidney only differ with regard to their glycosylation but not with regard to their amino acid sequence.

In a preferred embodiment a tns-AP is used as an unglycosylated tns-AP to produce the conjugate according to the invention which can be obtained by recombinant expression of a nucleic acid coding for tns-AP in a prokaryotic cell, preferably in E. coli, and optionally after naturation. Such processes for producing recombinant proteins in prokaryotes are known from the prior art (cf. Lilie et al., supra).

It is also preferred to use a dextran for the conjugate having an average molecular weight of 10–500 kDa. However, it has turned out that the molecular weight of the dextran that is used only has a very slight influence on the properties of the inventive conjugate. Dextran can be coupled to tns-AP by known methods. For this the dextran is firstly activated, preferably by periodate oxidation of dextran, cyanylation with CNBr or activation with CDAP (1-cyano-dimethylaminopyridinium tetra-fluoroborate). Subsequently it is coupled by incubation preferably at room temperature (cf. e.g. Andersson, A., et al., Int. J. Cancer 47 (1991) 439–444; Holmberg, A. and Meurling, L., Bioconjug. Chem. 4 (1993) 570–573; Lovqvist, A., et al., Cancer Biother. 8 (1993) 345–356; Olsson, P., et al., Int. J. Cancer 56 (1994) 529–537; Sjostrom, A., et al., Int. J. Cancer 70 (1997) 383–389). After stopping the reaction, preferably with an amine reagent, the conjugate can be isolated by known purification methods such as chromatographic methods. Dextran is covalently bound to the unglycosylated tns-AP at random positions by this method which results in a heterogeneous mixture of conjugates of dextran and tns-AP. The suitability of the conjugate according to the invention is ensured by the fact that reproducible conditions are adhered to for the production with regard to temperature, activation reagent, ratio of activation reagent to dextran, ratio of unglycosylated tns-AP to activated dextran, average molecular weight of the dextran, incubation time and stop reagent. The suitable reaction conditions according to the invention can, however, also be varied over a wide range and are uncritical.

The reaction is preferably carried out at room temperature and for about one hour. CDAP or CNBr are preferably used as activation reagents. The weight ratio of activation reagent to dextran is preferably 1:2 to 1:20.

It is preferable to use activated dextran in an excess in order to produce the conjugate according to the invention preferably in a molar ratio of 1:2 to 1:500, particularly preferably 1:10 to 1:500 (unglycosylated tns-AP to dextran).

Another subject matter of the invention is a process for producing a conjugate by reacting unglycosylated tns-AP with activated dextran by incubation in an aqueous solution, stopping the reaction and isolating the conjugate from the solution. The incubation period is preferably about one hour. The reaction is preferably terminated by adding an amine reagent such as ethanolamine.

In a preferred embodiment unglycosylated tns-AP which has been obtained by recombinant expression of a nucleic acid coding for tns-AP in a prokaryotic cell is used to produce the conjugate according to the invention.

A dextran having an average molecular weight of 10–100 kDa is particularly preferably used, the dextran is activated with CDAP, and unglycosylated tns-AP and activated dextran are used for the said reaction in a molar ratio of 1:10 to 1:500.

Another subject matter of the invention is the use of an unglycosylated tns-AP to produce a conjugate according to the invention consisting of unglycosylated tns-AP and dextran.

Another subject matter of the invention is the use of a conjugate according to the invention as a standard in a method for the quantitative determination of alkaline phosphatase. Such methods are described for example by Tietz et al., supra.

The following examples, publications, the sequence protocol and the figures elucidate the invention further, the protective scope of which derives from the patent claims. The described methods are to be understood as examples which still describe the subject matter of the invention even after modifications.

EXAMPLE 1

Cloning the Human tns-AP Gene

This section describes the isolation and cloning of the gene for human tns-AP and the construction of a fusion gene with a PelB signal sequence suitable for the expression in Escherichia coli. All DNA amplification and cloning techniques used for this are well known to a person skilled in the art and are described in Sambrook, J., et al., "Molecular Cloning: A Laboratory Manual" (1989), Eds. J. Sambrook, E. F. Fritsch and T. Maniatis, Cold Spring Harbour Laboratory Press, Cold Spring Harbour, N.Y.

Figure 1:
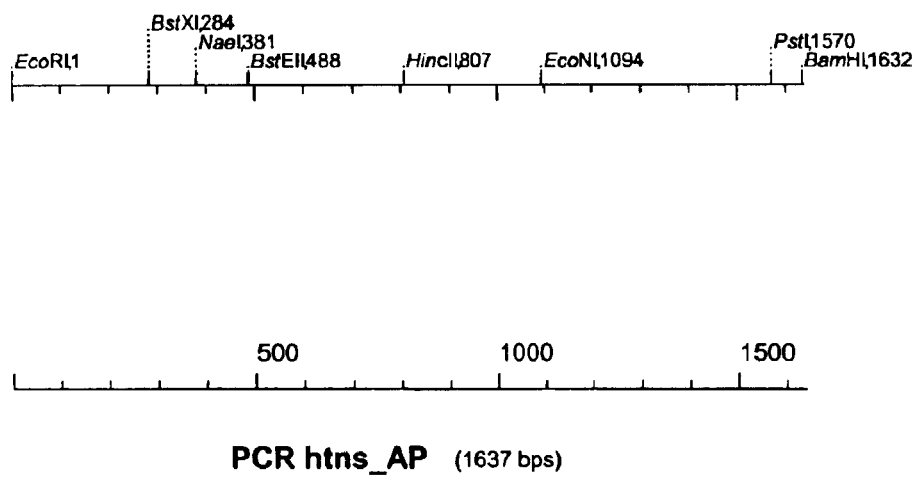
FIG. 1 restriction map of human tns-AP

Firstly the complete gene sequence for human tns-AP as well as the directly neighbouring 5' and 3' regions were isolated by means of the so-called polymerase chain reaction (SEQ ID NO: 3 and 4), FIG. 1) from a human liver cDNA bank using the oligonucleotides apNup (SEQ ID NO: 1) and apCdw (SEQ ID NO: 2). Subsequently the PCR product was digested with the restriction endonucleases EcoRI and BamHI and ligated in an expression vector that had been cleaved with the same enzymes. The resulting plasmid is shown in FIG. 2 (pBKShuap11).

Figure 3:
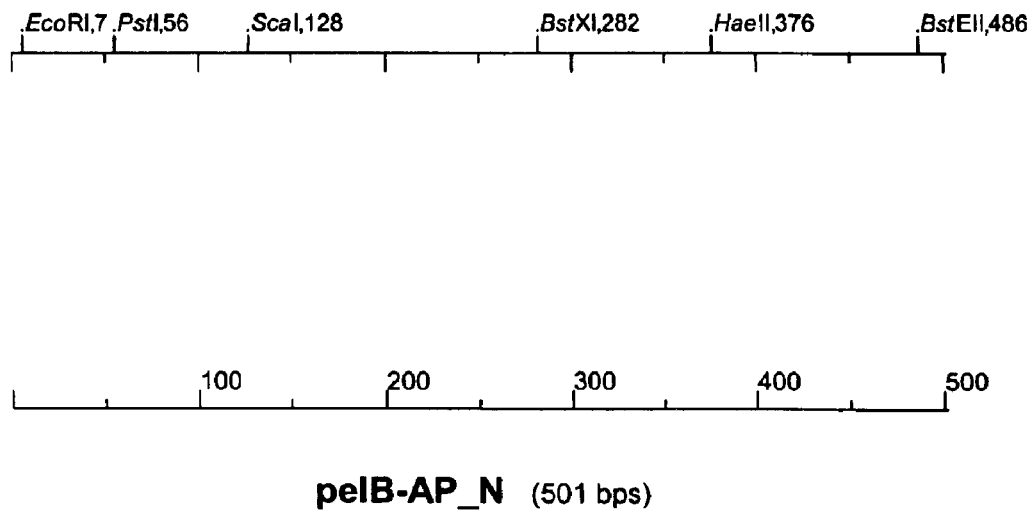
FIG. 3 restriction map of pelB-APN

The fusion gene used for the expression was subsequently constructed by the following three steps: [I] A synthetic gene section was constructed by gene synthesis which fused a region encoding the PelB signal sequence to a part of the region that encodes the tns-AP gene (positions 102–503 of SEQ ID NO:3). The synthesis was carried out in a 3-step PCR reaction by means of eight (SEQ ID NO: 5–12) oligonucleotides overlapping by 20 bp, wherein in the first step gene segments of the primer pairs uppel/dwpel (fragment 1), apn1_up/apn1_dw (fragment 2), apn2_up/apn2dw (fragment 3) and apn3_up/apn3_dw (fragment 4) were prepared. In the second step fragments 1 and 2 were used as the template to synthesize fragment 5 in which the oligonucleotides uppel and apn1_dw served as primers and the fragments 3 and 4 were used to prepare fragment 6 in which the oligonucleotides apn2_up and apn3_dw served as primers. In the third step fragments 5 and 6 were used as the template to synthesize the final synthetic gene pelB-AP_N (SEQ ID NO: 13, FIG. 3) in which the oligonucleotides uppel and apn3_dw were used as primers. Identical amount of primers and fragments were used for the synthesis in each of the three steps of the synthesis.

Figure 2:
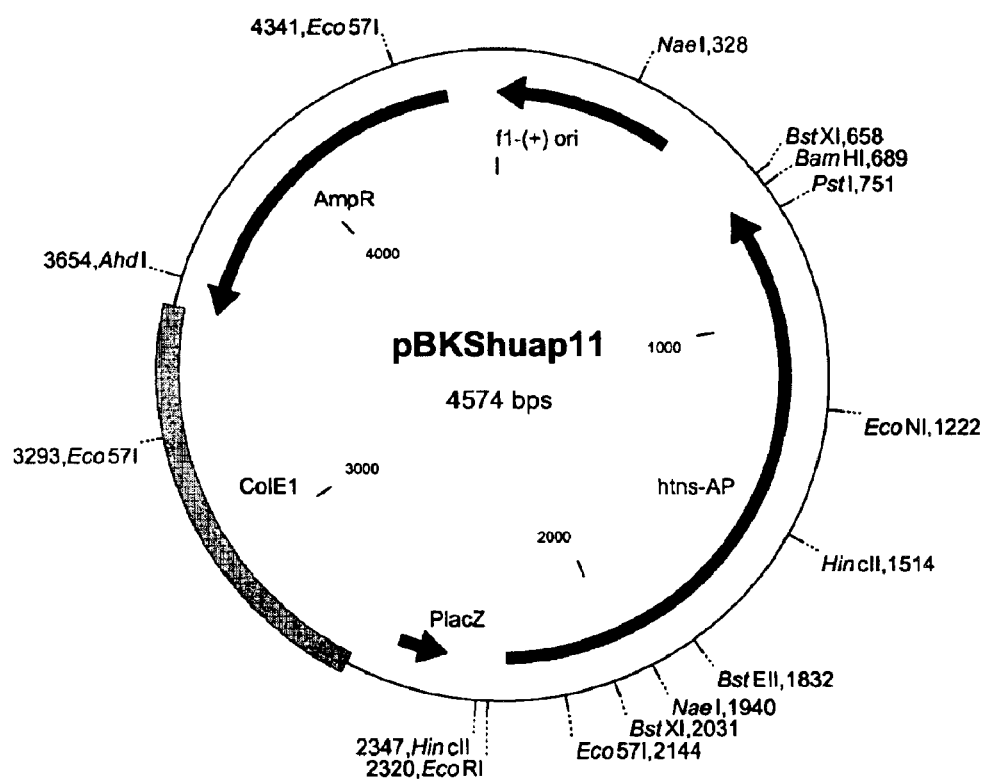
FIG. 2 plasmid map of pBKShuap 11

[II] A section of the htns-AP gene (bp 102–1561 of SEQ ID NO: 3) was amplified using the oligonucleotides mhua-pQEup (SEQ ID NO: 14) and mhuapQEdw (SEQ ID NO: 15) as primers in a polymerase chain reaction using the plasmid according to FIG. 2 as template. The oligonucleotide mhuapQEdw removes the sequence coding for the last 20 amino acids of htns-AP and adds the sequence AGATCT-TAGTAAGGATCCAGAT (SEQ ID NO: 18) to the 3' end of the gene.

Figure 4:
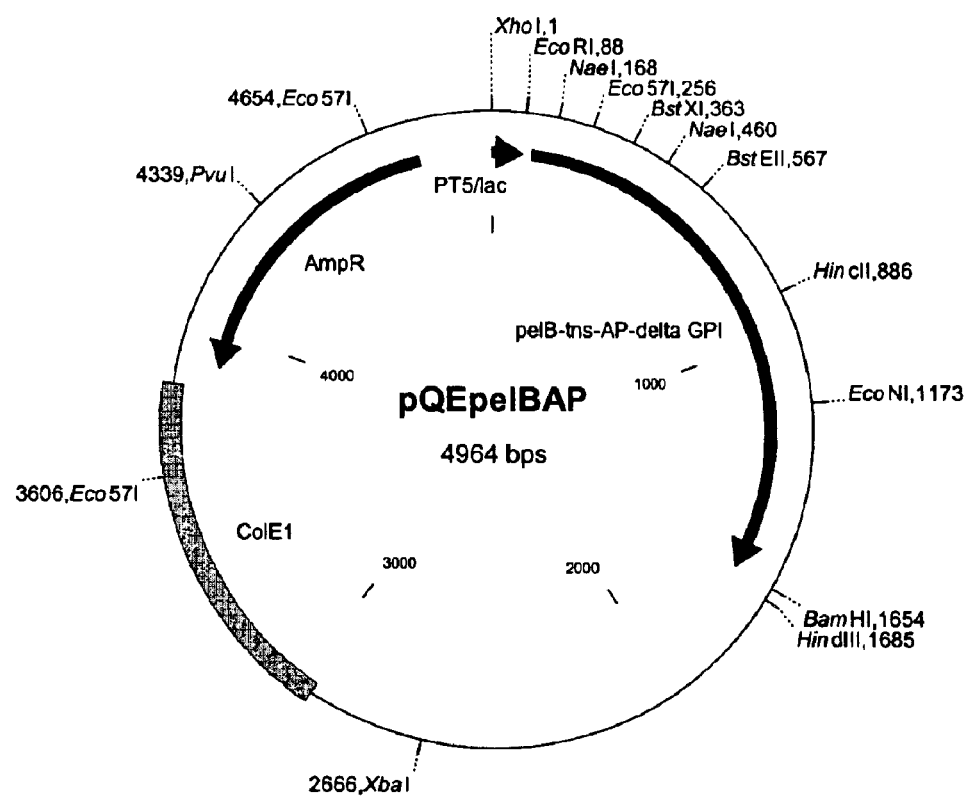
FIG. 4 plasmid map pQ Epel BAP

[III] The synthetic gene pelB-AP_N was digested with the restriction endonucleases EcoRI and BstEII, the gene segment from step [II] was digested with the restriction endonucleases BstEII and BamHI and ligated with the plasmid pQE60 (Qiagen, Hilden, Germany) that had been digested with the restriction endonucleases EcoRI and BamHI. Equal amounts of the DNA fragments used were used for the ligation reaction. The resulting fusion gene or fusion protein was named pelB-tns-AP-deltaGPI (SEQ ID NO: 16 and 17), the resulting expression plasmid in which the expression of the pelB-tns-AP fusion protein is under the control of the IPTG-inducible T5 promoter is named pQE-pelBAP (FIG. 4).

EXAMPLE 2

Expression of the pelB-tns-AP Gene in *Escherichia coli*

E. coliK12 was transformed with the expression plasmid from example 1 pQEpelBAP and the resulting strain was cultured in LB medium containing ampicillin. The pelB-tns-AP fusion protein was expression after addition of IPTG in the middle of the logarithmic growth phase. The cells are harvested by centrifugation after a suitable expression phase (3–12 h).

EXAMPLE 3

IB Isolation, Solubilization and Refolding

| Buffer 1: | 10 mM Tris-HCl, pH 8.0 |
|---|---|
| Buffer 2: | 8 M urea, 10 mM DTT, 100 mM Tris-HCl, pH 8.0 |
| Buffer 3: | 200 mM Tris-HCl, 40 mM $MgCl_2$, 0.1 mM $ZnCl_2$, 9 mM GSH, 4 mM GSSG, 40% (w/v) glycerol, pH 8.0 |

(DDT: dithiothreitol,
GSH: reduced glutathione,
GSSG: oxidized glutathione)

IB Isolation

The tns-AP fusion protein is formed intracellularly in two forms: i) a small proportion (>5%) is present as a soluble, biologically active enzyme the activity of which can be determined by the method described by Bretaudiere & Spillmann (1984) Methods of Enzymatic Analysis, VCH, 75–82); ii) the major proportion is produced in the form of enzymatically inactive IBs. These IBs have to be isolated before solubilizing, renaturing, purifying and modifying the protein. For this the cells are taken up in buffer 1 and lysed by means of high pressure dispersion. Afterwards the IBs are isolated by several centrifugation and washing steps (in buffer 1).

Solubilization

The IBs are solubilized by stirring continuously for 2 hours at room temperature in buffer 2 containing 25 mg IBs (wet weight) per ml buffer 2. Subsequently non-solubilized protein is removed by centrifugation to prepare a clear solubilisate.

Refolding

Figure 5:
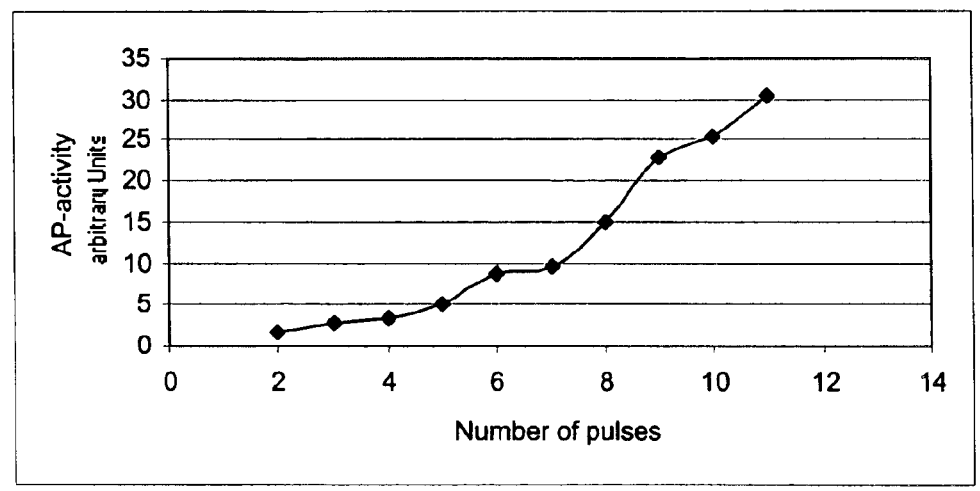
FIG. 5 refolding kinetics of unglycosylated tns-AP

The protein is refolded in buffer 3. For this the clear solubilisate having a final concentration of 9.6 $\mu g/ml$ (protein determination according to Bradford, M. M., Analytical Biochemistry 72 (1976) 248–254) is transferred dropwise into buffer 3 while stirring constantly. This process (pulsing) is repeated 12 times at intervals of 24 hours. The enzymatic activity is determined in the refolding mixture using p-nitrophenyl phosphate as the substrate according to the method of Bretaudiere & Spillmann, ((1984) Methods of Enzymatic Analysis, VCH, 75–82) in each case 24 h after addition of the clear solubilisate; the result of a typical refolding reaction is shown in FIG. 5. The refolding mixture is centrifuged 24 hours after the last addition of the clear solubilisate in order to remove insoluble protein aggregates, afterwards the active tns-AP is located in the supernatant.

EXAMPLE 4

Purification and Dextranization of the pelB-tns-AP Fusion Gene

| Buffer 4: | 20 mM Tris-HCl, pH 8.0 |
|---|---|
| | 2 mM $MgCl_2$ |
| | 0.1 mM $ZnCl_2$ |
| | 100 mM NaCl |

The supernatant from example 3 containing the active tns-AP is firstly concentrated by ultrafiltration over an ultrafiltration membrane made of regenerated cellulose having an exclusion size of 10 kDa. In order to avoid loss of tns-AP by unspecific binding to the membrane, this can firstly be incubated for 24 h in a 1% bovine serum albumin solution.

Subsequently the mixture is dialysed by flow dialysis for 24 h against buffer 4. The conductivity of the dialysis buffer is adjusted to 13.2 mS/cm, the flow rate is 20 liters buffer 4/h. The protein aggregates that form after dialysis are removed by centrifugation.

The dialysate is then concentrated to about a tenth of the initial volume by an ultrafiltration as already described above. Subsequently the protein content of the solution and the activity of tns-AP is determined as described. The protein pretreated in this manner can then be chemically modified by reaction with dextran.

For this 1 g dextran T-40 (average molecular weight 40 kDa) is dissolved in 20 ml distilled water and cooled to 4° C. After adding 200 mg CDAP bromide, 800 µl of a 0.6 M triethanolamine solution is added dropwise to the solution. The pH of this solution is adjusted to 8 with 1 M $KH_2PO_4$ (solution 5).

Figure 6:
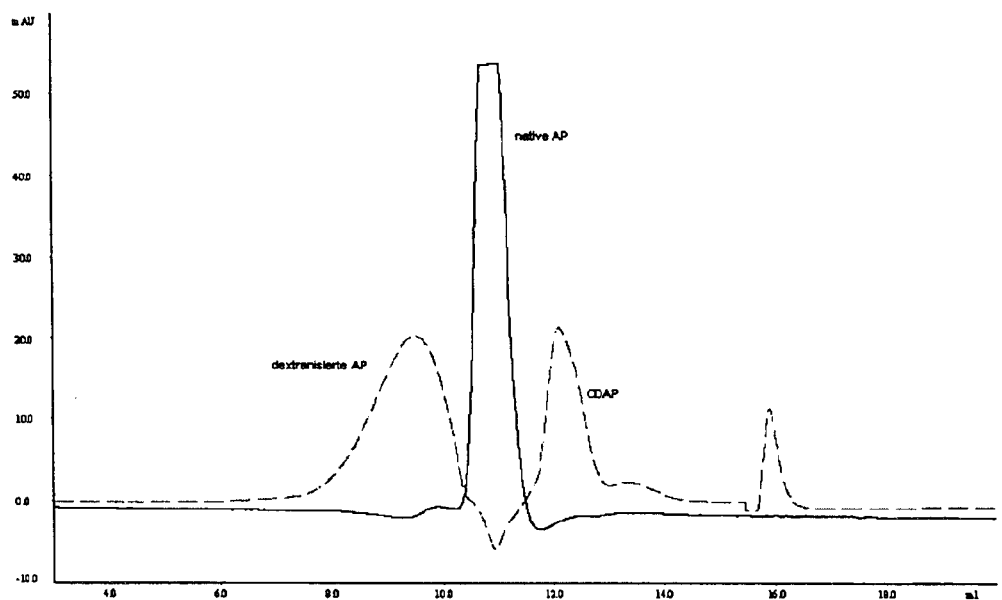
FIG. 6 elution profile of dextranized tns-AP (the figure shows the elution profile of dextranized AP (dextran of 40 kDa) in comparison to native AP)

For dextranization 1.5 mg tns-AP is incubated with 300 µl solution 5 for 1 h at room temperature. The reaction is then stopped by addition of 12.5 µl of a 1 M ethanolamine solution and incubated again for 30 min at room temperature. This is followed by a 24 hour dialysis against buffer 4. The result of the dextranization is checked by gel chromatography on a TSKG 5000 PWXL column (Tosohaas) using 200 mM potassium phosphate buffer, pH 8.0 as the mobile buffer; a typical elution profile of the tns-AP before and after dextranization is shown in FIG. 6. The enzymatic activity of tns-AP after dextranization is ca. 70–90% of the activity before the dextranization.

In an analogous manner tns-AP is coupled to dextran with an average molecular weight of 40 kDa, 60 kDa, 188 kDa and 400 kDa.

EXAMPLE 5

Evaluation of Dextranized tns-AP in a Clinical Activity Test

The refolded, dextranized protein is evaluated with regard to its suitability as a reference enzyme by a method comparison in two of the buffer systems published by the International Federation of Clinical Chemistry and Laboratory Medicine (IFCC) (Tietz, N. W., et al., J. Clin. Chem. Clin. Biochem. 21 (1983) 731–748). This test is carried out at 37° C. using p-nitrophenyl phosphate as the substrate. In this method comparison the activity of AP in a human serum lies exactly on the line of bisection of the x/y diagram (abscissa: activity in 350 mM AMP, pH 10.5; ordinate 900 mM AMP, pH 10.44), i.e. the AP mixture present in serum has an identical enzymatic-specific activity in both buffer systems. A suitable reference enzyme should ideally have the same properties.

Figure 7:
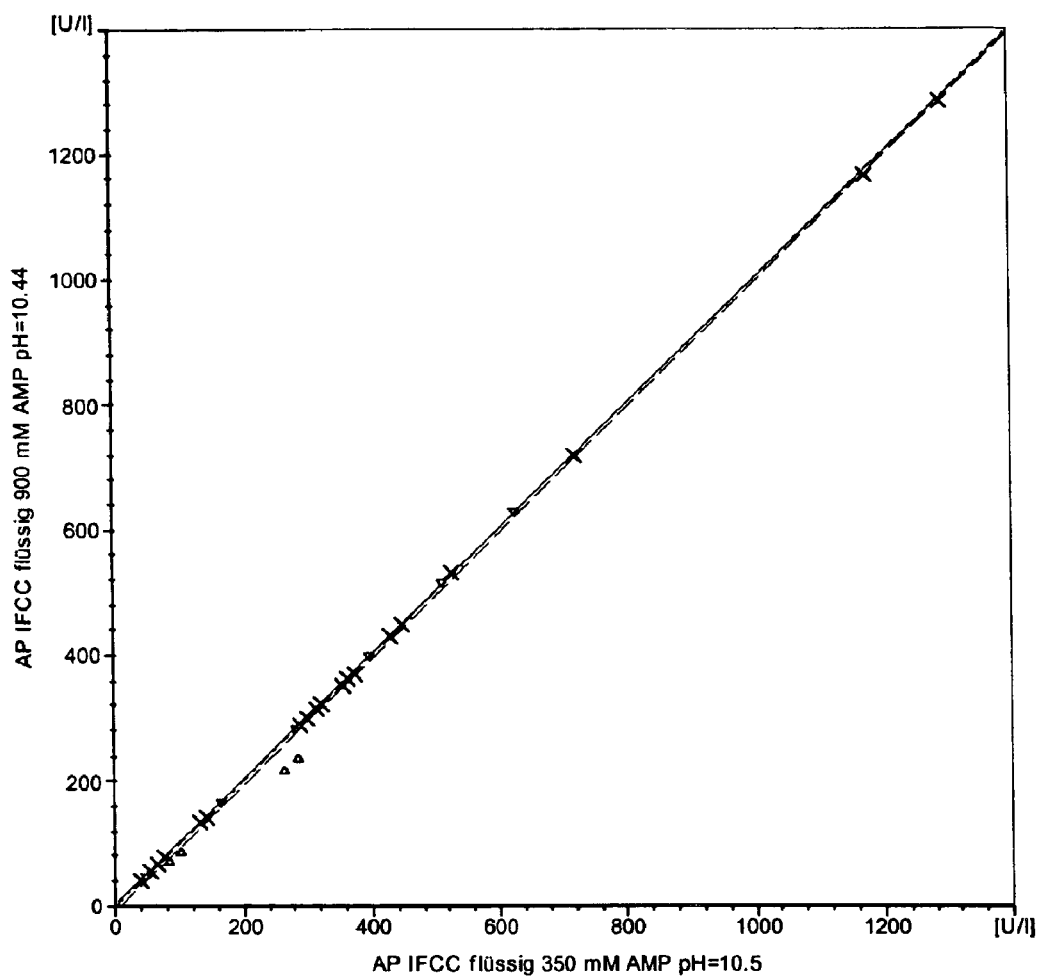
FIG. 7 activity profile of dextranized tns-AP (dextran of 40 kDa) (x: results with serum samples; Δ: results with standard according to the invention; ∇=results with control sera (PNU=Precinorm U, Roche Diagnostics GmbH, Mannheim, PPU=Precipath U, Roche Diagnostics GmbH, Mannheim)
Figure 8:
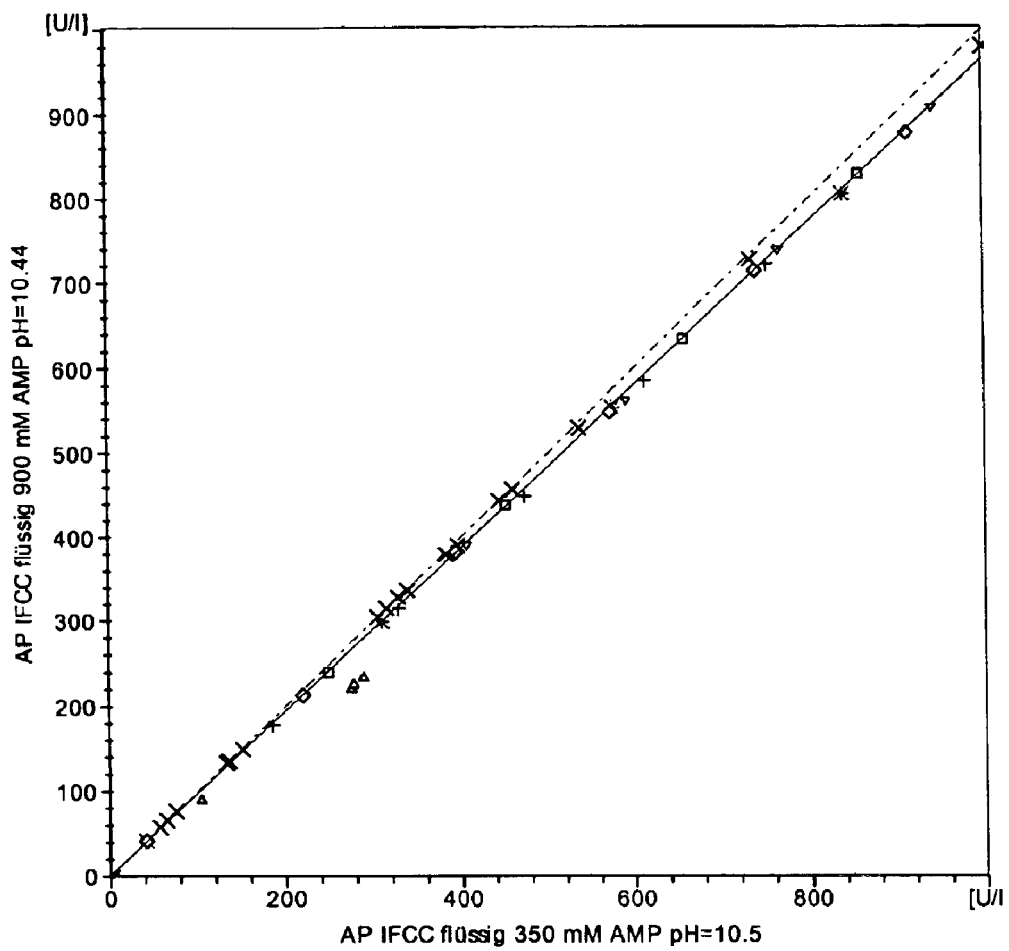
FIG. 8 activity profile of dextranized tns-AP (dextran of 10 kDa, 40 kDa, 60 kDa, 188 kDa, 400 kDa=AP 1 10 000, etc.) in comparison with serum samples (=human sera) and control sera (PNU=Precinorm U, Roche Diagnostics GmbH, Mannheim, PPU=Precipath U, Roche Diagnostics GmbH, Mannheim=controls)

The evaluation comprised testing the activity of the dextranized tns-AP from example 4, the AP activity in human sera and the AP activity in commercial control sera (PNU, PPU, Roche Diagnostics GmbH, Mannheim, Germany) in the described method comparison; they were evaluated on a Roche/Hitachi analyser (Roche Diagnostics GmbH, Mannheim, Germany). Typical evaluation profiles are shown in FIGS. 7 and 8: The activity profile of the dextranized tns-AP is identical to that of the human serum and lies on the line of bisection of the x/y diagram, i.e. both samples have the same activity in both buffers. Hence dextranized tns-AP fulfils the requirements for an ideal control enzyme. In this case the molecular weight of the dextran obviously has no influence on the activity profile (cf. FIG. 8). In contrast the AP activity in the control sera lies below the line of bisection (FIG. 7).

EXAMPLE 6

Glucosylation of tns-AP

Tns-AP was prepared according to example 3 and purified according to example 4. It was non-enzymatically derivatized with glucose (glucosylation) by incubating the protein in the presence of an excess of 1-α-D-glucopyranoside. The non-enzymatic glucosylation of proteins is carried out in the presence of reducing sugars on free amino groups of a protein by the so-called Maillard-Reaction (Reddy, S., et al., Biochemistry 34 (1995) 10872–10878; Thornalley, P. J., et al., Biochem. J. 344 (1999) 109–116; Singh, R., et al., Diabetologia 44 (2001) 129–146). For this 1.6 and 9.1 µmol of recombinant alkaline phosphatase in 50 mM HEPES buffer, pH 8.0 are incubated for 24 h at 4° C. in the presence of a 1000-fold excess of 1-α-D-gluco-pyranoside. The glucosylation of the alkaline phosphatase is indicated by the subsequent increase in the molecular weight of the protein that is detected by means of MALDI-TOF. The enzymatic activity is determined using the method cited in example 3 which shows that the enzyme still has 90–98% of the initial activity after the non-enzymatic glucosylation. The enzyme preparation prepared in this manner is then used and evaluated in the clinical activity test described in example 5.

Figure 9:
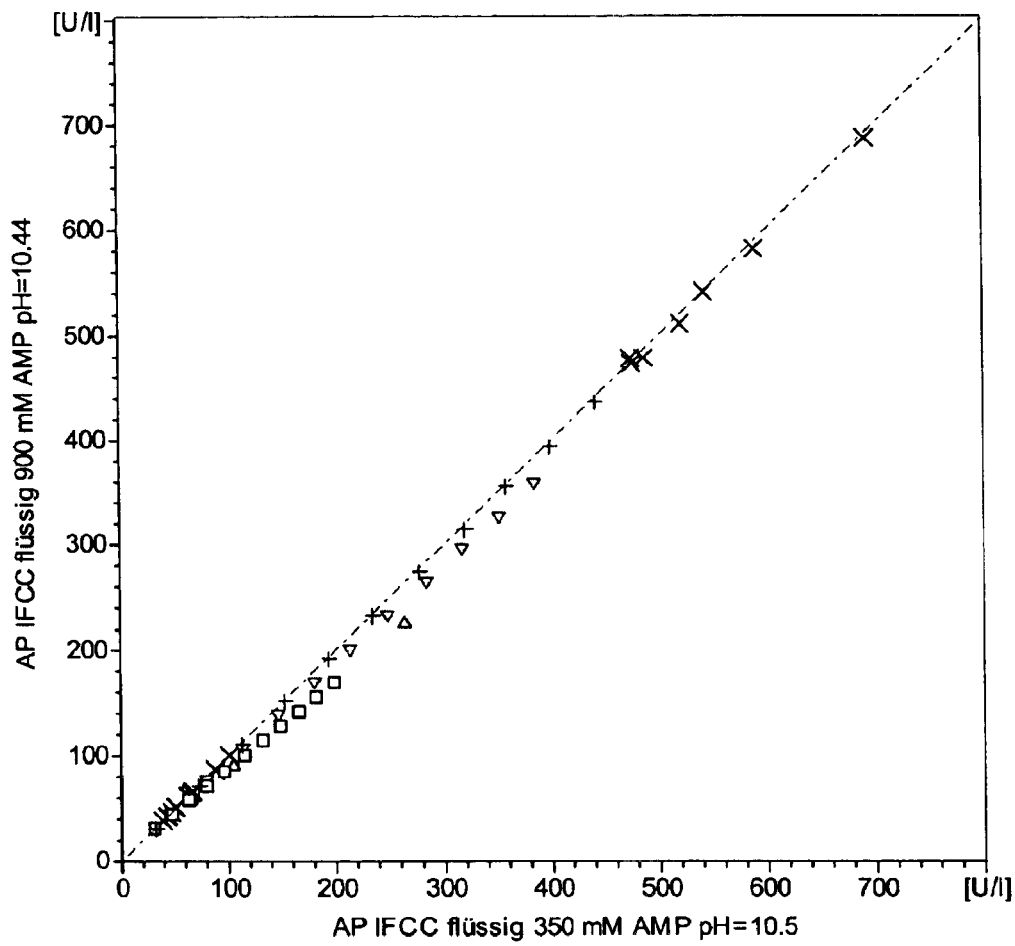
FIG. 9 activity profile of dextranized tns-AP (40 kDa) compared to serum samples, to glucosylated tns-AP, control sera (PNU, PPU) and unmodified, nonglycosylated tns-AP (native AP)

The dextranized AP according to the invention lies exactly on the line of bisection. In contrast the non-dextranized AP, the glucosylated AP and the tns-AP contained in commercial control sera lie below the line of bisection (FIG. 9). In contrast to dextranized tns-AP, all other APs that were tested do not fulfil the requirements for an ideal calibrator.

List of References

Andersson, A., et al., Int. J. Cancer 47 (1991) 439–444
Balbas, P., Mol. Biotechnol. 19 (2001) 251–267
Bradford, M. M., Analytical Biochemistry 72 (1976) 248–254
Bretaudiere & Spillmann, ((1984) Methods of Enzymatic Analysis, VCH, 75–82)
Fukushi, M., et al., Biochem. Biophys. Res. Commun. 246 (1998) 613–618
Harris, J., Clin. Chim. Acta 186 (1990) 133–150
Holmberg, A., and Meurling, L., Bioconjug. Chem. 4 (1993) 570–573
Hooper, N. M., Clin. Chim. Acta 266 (1997) 3–12
Lilie, H., et al., Curr. Opin. Biotechnol. 9 (1998) 497–501
Lovqvist, A., et al., Cancer Biother. 8 (1993) 345–356
Makrides, S. C., Microbiol. Rev. 60 (1996) 512–538
Maldonado, O., et al., J. Clin. Gastroenterol. 27 (1998) 342–345
McComb, et al., (1979), Alkaline Phosphatases, Plenum Press, New York
Miura, M., et al., Ann. Clin. Biochem. 31 (1994) 25–30
Moss, D. W., Clin. Chem. 38 (1992) 2486–2492
Mulivor, R. A., et al., J. Lab. Clin. Med. 105 (1985) 342–348
Nosjean, O., et al., Biochem. J. 321 (1997) 297–303
Oda, K., et al., J. Biochem. (Tokyo) 126 (1999) 694–699
Olsson, P., et al., Int. J. Cancer 56 (1994) 529–537
Reddy, S., et al., Biochemistry 34 (1995) 10872–10878
Romagnoli, E., et al., Clin. Chem. Lab. Med. 36 (1998) 163–168
Sambrook, J., et al., in "Molecular Cloning: A Laboratory Manual" (1989), Eds. J.
Sambrook, E. F. Fritsch and T. Maniatis, Cold Spring Harbour Laboratory Press, Cold Spring Harbour, N.Y.
Silve, C., Curr. Opin. Rheumatol. 6 (1994) 336–339
Singh, R., et al., Diabetologia 44 (2001) 129–146

Sjostrom, A., et al., Int. J. Cancer 70 (1997) 383–389
Thornalley, P. J., et al., Biochem. J. 344 (1999) 109–116
Tietz, N. W., et al., J. Clin. Chem. Clin. Biochem. 21 (1983) 731–748 U.S. Pat. No. 5,434,067
Weiss, M. J., et al., J. Biol. Chem. 263 (1988) 12002–12010
Weiss, M. J., et al., Proc. Natl. Acad. Sci. USA 83 (1986) 7182–7186
Wiwanitkit, V., BMC Fam. Pract. 2 (2001) 2

---

What is claimed is:

1. A conjugate comprising an unglycosylated tissue non-specific alkaline phosphatase (tns-AP) comprising amino acids 18–504 of SEQ ID NO:4 and dextran.

2. The conjugate of claim 1, wherein the tns-AP is obtained by recombinant expression of a nucleic acid coding for tns-AP in a prokaryotic cell.

3. The conjugate of claim 1 or 2, wherein the dextran has an average molecular weigh of 10–500 kDa.

4. A method for producing a conjugate comprising reacting an unglycosylated tns-AP comprising amino acids 18–504 of SEQ ID NO:4 with activated dextran by incubation in an aqueous solution, stopping the reaction and isolating the conjugate from the solution.

5. The method of claim 4, wherein the tns-AP is obtained by recombinant expression of a nucleic acid coding for the tns-AP in a prokaryotic cell.

6. The method of claim 4 or 5, wherein the dextran has an average molecular weight of 10–500 kDa.

7. The method of claim 4 or 5, wherein the activated dextran is activated with CDAP or CNBr.

8. The method of claim 4 or 5, wherein the unglycosylated tns-AP and the activated dextran are used for the said reaction in a ratio of 1:2 to 1:500.

9. A method for quantitating alkaline phosphatase activity comprising:
   a) obtaining a serum sample from a patient;
   b) determining alkaline phosphatase activity in the serum sample;
   c) comparing the alkaline phosphatase activity in the serum sample to a standard comprising a conjugate comprising an unglycosylated tissue non-specific alkaline phosphatase comprising amino acids 18–504 of SEQ ID NO:4 and dextran; and
   d) quantitating alkaline phosphatase activity in the serum sample based on the comparison.

* * * * *

SEQUENCE LISTING

```
<160> NUMBER OF SEQ ID NOS: 18

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence:primer apNup

<400> SEQUENCE: 1
cacagaattc tgcatctctg ggctccaggg ataaagcagg tc                         42

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:primer apCdw

<400> SEQUENCE: 2
tctggatccg ggccctcaga acaggacgct c                                     31

<210> SEQ ID NO 3
<211> LENGTH: 1637
<212> TYPE: DNA
<213> ORGANISM: Homo sapiens
<220> FEATURE:
<223> OTHER INFORMATION: hutns-AP, pcr-product

<400> SEQUENCE: 3
gaattctgca tctctgggct ccagggataa agcaggtctt ggggtgcacc atgatttcac      60
cattcttagt actggccatt ggcacctgcc ttactaactc cttagtgcca gagaaagaga     120 aagacccaa gtactggcga gaccaagcgc aagagacact gaaatatgcc ctggagcttc      180
agaagctcaa caccaacgtg gctaagaatg tcatcatgtt cctgggagat gggatgggtg     240
tctccacagt gacggctgcc cgcatcctca ggtcagct ccaccacaac cctggggagg       300
agaccaggct ggagatggac aagttcccct tcgtggccct ctccaagacg tacaacacca     360
atgcccaggt ccctgacagc gccggcaccg ccaccgccta cctgtgtggg gtgaaggcca     420
atgagggcac cgtgggggta agcgcagcca ctgagcgttc ccggtgcaac accacccagg     480
ggaacgaggt cacctccatc ctgcgctggg ccaaggacgc tgggaaatct gtgggcattg     540
tgaccaccac gagagtgaac catgccaccc cagcgccgc ctacgcccac tcggctgacc      600
gggactggta ctcagacaac gagatgcccc ctgaggcctt gagccagggc tgtaaggaca     660
tcgcctacca gctcatgcat aacatcaggg acattgacgt gatcatgggg ggtggccgga     720
aatacatgta ccccaagaat aaaactgatg tggagtatga gagtgacgag aaagccaggg     780
gcacgaggct ggacggcctg gacctcgttg acacctggaa gagcttcaaa ccagacaca      840 agcactccca cttcatctgg aaccgcacgg aactcctgac ccttgacccc cacaatgtgg     900
actacctatt gggtctcttc gagccggggg acatgcagta cgagctgaac aggaacaacg     960
tgacggaccc gtcactctcc gagatggtgg tggtggccat ccagatcctg cggaagaacc    1020
ccaaaggctt cttcttgctg gtggaaggag gcagaattga ccacgggcac catgaaggaa    1080
```

-continued

```
aagccaagca ggccctgcat gaggcggtgg agatggaccg ggccgtcggg caggcaggca    1140
gcttgacctc ctcggaagac actctgaccg tggtcactgc ggaccattcc cacgtcttca    1200
catttggtgg atacacccc cgtggcaact ctatctttgg tctggccccc atgctgagtg     1260
acacagacaa gaagcccttc actgccatcc tgtatggcaa tgggcctggc tacaaggtgg    1320
tgggcggtga acgagagaat gtctccatgg tggactatgc tcacaacaac taccaggcgc    1380
agtctgctgt gccctgcgc acgagaccc acggcgggga ggacgtggcc gtcttctcca      1440
agggccccat ggcgcacctg ctgcacggcg tccacgagca gaactacgtc ccccacgtga    1500
tggcgtatgc agcctgcatc ggggccaacc tcggccactg tgctcctgcc agctcggcag    1560
gcagccttgc tgcaggcccc ctgctgctcg cgctggccct ctaccccctg agcgtcctgt    1620
tctgagggcc cggatcc                                                   1637
```

<210> SEQ ID NO 4
<211> LENGTH: 524
<212> TYPE: PRT
<213> ORGANISM: Homo sapiens
<220> FEATURE:
<223> OTHER INFORMATION: hutns-AP, protein

<400> SEQUENCE: 4

```
Met Ile Ser Pro Phe Leu Val Leu Ala Ile Gly Thr Cys Leu Thr Asn
  1               5                   10                  15

Ser Leu Val Pro Glu Lys Glu Lys Asp Pro Lys Tyr Trp Arg Asp Gln
             20                  25                  30

Ala Gln Glu Thr Leu Lys Tyr Ala Leu Glu Leu Gln Lys Leu Asn Thr
         35                  40                  45

Asn Val Ala Lys Asn Val Ile Met Phe Leu Gly Asp Gly Met Gly Val
     50                  55                  60

Ser Thr Val Thr Ala Ala Arg Ile Leu Lys Gly Gln Leu His His Asn
 65                  70                  75                  80

Pro Gly Glu Glu Thr Arg Leu Glu Met Asp Lys Phe Pro Phe Val Ala
                 85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255
```

-continued

```
Lys Ser Phe Lys Pro Arg His Lys His Ser His Phe Ile Trp Asn Arg
            260                 265                 270

Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
            290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Val Gly Gln Ala Gly Ser Leu Thr Ser Ser
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
    450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 5
<211> LENGTH: 80
<212> TYPE: DNA
<213> ORGANISM: Artificial Sequence
<220> FEATURE:
<223> OTHER INFORMATION: Description of Artificial Sequence:primer
      APN1_up

<400> SEQUENCE: 5
atccgaagta ctggcgagac caagcgcaag agacactgaa atatgccctg gagcttcaga      60
agctcaacac caacgtggct                                                  80

<210> SEQ ID NO 6
<211> LENGTH: 80
<212> TYPE: DNA
<213> ORGANISM: Artificial Sequence
<220> FEATURE:
<223> OTHER INFORMATION: Description of Artificial Sequence:primer
      APN2_up

<400> SEQUENCE: 6
ccacagtgac ggctgcccgc atcctcaagg gtcagctcca ccacaaccct ggggaggaga      60
```

```
ccaggctgga gatggacaag                                              80

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence:primer
      APN3_up

<400> SEQUENCE: 7
cccaggtccc tgacagcgcc ggcaccgcca ccgcctacct gtgtggggtg aaggccaatg    60
agggcaccgt gggggtaagc                                               80

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence:primer
      APN1_dw

<400> SEQUENCE: 8
gcgggcagcc gtcactgtgg agacacccat cccatctccc aggaacatga tgacattctt    60
agccacgttg gtgttgagct                                               80

<210> SEQ ID NO 9
<211> LENGTH: 80
<212> TYPE: DNA
<213> ORGANISM: Artificial Sequence
<220> FEATURE:
<223> OTHER INFORMATION: Description of Artificial Sequence:primer
      APN2_dw

<400> SEQUENCE: 9
ggcgctgtca gggacctggg cattggtgtt gtacgtcttg gagagggcca cgaaggggaa    60
cttgtccatc tccagcctgg                                               80

<210> SEQ ID NO 10
<211> LENGTH: 80
<212> TYPE: DNA
<213> ORGANISM: Artificial Sequence
<220> FEATURE:
<223> OTHER INFORMATION: Description of Artificial Sequence:APN3_dw

<400> SEQUENCE: 10
caggatggag gtgacctcgt tcccctgggt ggtgttgcac cgggaacgct cagtggctgc    60
gcttaccccc acggtgccct                                               80

<210> SEQ ID NO 11
<211> LENGTH: 80
<212> TYPE: DNA
<213> ORGANISM: Artificial Sequence
<220> FEATURE:
<223> OTHER INFORMATION: Description of Artificial Sequence:primer uppel

<400> SEQUENCE: 11
cacacagaat tcattaaaga ggagaaatta actatgaaat atctgctgcc aactgctgca    60
gctggtctgc tgctcctggc                                               80

<210> SEQ ID NO 12
<211> LENGTH: 81
<212> TYPE: DNA
```

<213> ORGANISM: Artificial Sequence
<220> FEATURE:
<223> OTHER INFORMATION: Description of Artificial Sequence:primer dwpel

<400> SEQUENCE: 12
gtctcgccag tacttcggat ctttttcttt ttctggaacc agtgccatag ccggctgagc    60
agccaggagc agcagaccag c                                              81

<210> SEQ ID NO 13
<211> LENGTH: 501
<212> TYPE: DNA
<213> ORGANISM: Artificial Sequence
<220> FEATURE:
<223> OTHER INFORMATION: Description of Artificial Sequence:pelB-AP_N

<400> SEQUENCE: 13
cacacagaat tcattaaaga ggagaaatta actatgaaat atctgctgcc aactgctgca    60
gctggtctgc tgctcctggc tgctcagccg gctatgcac tggttccaga aaagaaaaa    120 gatccgaagt actggcgaga ccaagcgcaa gagacactga atatgccct ggagcttcag    180 aagctcaaca ccaacgtggc taagaatgtc atcatgttcc tgggagatgg gatgggtgtc    240
tccacagtga cggctgcccg catcctcaag ggtcagctcc accacaaccc tggggaggag    300
accaggctgg agatggacaa gttccccttc gtggccctct ccaagacgta caacaccaat    360
gcccaggtcc ctgacagcgc cggcaccgcc accgcctacc tgtgtggggt gaaggccaat    420
gagggcaccg tggggtaag cgcagccact gagcgttccc ggtgcaacac cacccagggg    480
aacgaggtca cctccatcct g                                              501

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence:primer
    mhuapQEup

<400> SEQUENCE: 14
atatagaatt cttagtgcca gagaaagaga aagaccccaa g                        41

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence:primer
    mhuapQEdw

<400> SEQUENCE: 15
atctggatcc ttactaagat ctgcctgccg agctggcagg agcacag                  47

<210> SEQ ID NO 16
<211> LENGTH: 1539
<212> TYPE: DNA
<213> ORGANISM: Artificial Sequence
<220> FEATURE:
<223> OTHER INFORMATION: Description of Artificial Sequence:Fusionsgen
    pelB-tns-AP-deltaGPI

<400> SEQUENCE: 16
atgaaatatc tgctgccaac tgctgcagct ggtctgctgc tcctggctgc tcagccggct    60
atggcactgg ttccagaaaa agaaaaagat ccgaagtact ggcgagacca agcgcaagag    120

-continued

```
acactgaaat atgccctgga gcttcagaag ctcaacacca acgtggctaa gaatgtcatc    180
atgttcctgg gagatgggat gggtgtctcc acagtgacgg ctgcccgcat cctcaaggga    240
cagctccacc acaaccctgg ggaggagacc aggctggaga tggacaagtt ccccttcgtg    300
gccctctcca agacgtacaa caccaatgcc caggtccctg cagcgccgg caccgccacc    360
gcctacctgt gtgggtgaa ggccaatgag gcaccgtgg gggtaagcgc agccactgag    420
cgttcccggt gcaacaccac ccaggggaac gaggtcacct ccatcctgcg ctgggccaag    480
gacgctggga atctgtggg cattgtgacc accacgagag tgaaccatgc cacccccagc    540
gccgcctacg cccactcggc tgaccgggac tggtactcag acaacgagat gcccctgag    600
gccttgagcc agggctgtaa ggacatcgcc taccagctca tgcataacat cagggacatt    660
gacgtgatca tggggggtgg ccggaaatac atgtacccca agaataaaac tgatgtggag    720
tatgagagtg acgagaaagc caggggcacg aggctggacg gcctggacct cgttgacacc    780
tggaagagct tcaaaccgag acacaagcac tcccacttca tctggaaccg cacggaactc    840
ctgacccttg accccacaa tgtggactac ctattgggtc tcttcgagcc ggggacatg    900
cagtacgagc tgaacaggaa caacgtgacg gacccgtcac tctccgagat ggtggtggtg    960
gccatccaga tcctgcggaa gaaccccaaa ggcttcttct gctggtgga aggaggcaga    1020
attgaccacg gcaccatga aggaaaagcc aagcaggccc tgcatgaggc ggtggagatg    1080
gaccgggccg tcgggcaggc aggcagcttg acctcctcgg aagacactct gaccgtggtc    1140
actgcggacc attcccacgt cttcacattt ggtggataca ccccccgtgg caactctatc    1200
tttggtctgg ccccccatgct gagtgacaca gacaagaagc ccttcactgc catcctgtat    1260
ggcaatgggc ctggctacaa ggtggtgggc ggtgaacgag agaatgtctc catggtggac    1320
tatgctcaca caaactacca ggcgcagtct gctgtgcccc tgcgccacga gacccacggc    1380
ggggaggacg tggccgtctt ctccaagggc cccatggcgc acctgctgca cggcgtccac    1440
gagcagaact acgtccccca cgtgatggcg tatgcagcct gcatcggggc caacctcggc    1500
cactgtgctc ctgccagctc ggcaggcaga tcttagtaa                          1539
```

<210> SEQ ID NO 17
<211> LENGTH: 511
<212> TYPE: PRT
<213> ORGANISM: Artificial Sequence
<220> FEATURE:
<223> OTHER INFORMATION: Description of Artificial Sequence:Protein
      pelB-tns-AP-deltaGPI

<400> SEQUENCE: 17

Met Lys Tyr Leu Leu Pro Thr Ala Ala Gly Leu Leu Leu Ala
1               5                   10                  15

Ala Gln Pro Ala Met Ala Leu Val Pro Glu Lys Glu Lys Asp Pro Lys
                20                  25                  30

Tyr Trp Arg Asp Gln Ala Gln Glu Thr Leu Lys Tyr Ala Leu Glu Leu
            35                  40                  45

Gln Lys Leu Asn Thr Asn Val Ala Lys Asn Val Ile Met Phe Leu Gly
        50                  55                  60

Asp Gly Met Gly Val Ser Thr Val Thr Ala Ala Arg Ile Leu Lys Gly
65                  70                  75                  80

Gln Leu His His Asn Pro Gly Glu Glu Thr Arg Leu Glu Met Asp Lys
                85                  90                  95

Phe Pro Phe Val Ala Leu Ser Lys Thr Tyr Asn Thr Asn Ala Gln Val
                100                 105                 110

```
Pro Asp Ser Ala Gly Thr Ala Thr Ala Tyr Leu Cys Gly Val Lys Ala
            115                 120                 125

Asn Glu Gly Thr Val Gly Val Ser Ala Ala Thr Glu Arg Ser Arg Cys
        130                 135                 140

Asn Thr Thr Gln Gly Asn Glu Val Thr Ser Ile Leu Arg Trp Ala Lys
145                 150                 155                 160

Asp Ala Gly Lys Ser Val Gly Ile Val Thr Thr Thr Arg Val Asn His
                165                 170                 175

Ala Thr Pro Ser Ala Ala Tyr Ala His Ser Ala Asp Arg Asp Trp Tyr
            180                 185                 190

Ser Asp Asn Glu Met Pro Pro Glu Ala Leu Ser Gln Gly Cys Lys Asp
            195                 200                 205

Ile Ala Tyr Gln Leu Met His Asn Ile Arg Asp Ile Asp Val Ile Met
            210                 215                 220

Gly Gly Gly Arg Lys Tyr Met Tyr Pro Lys Asn Lys Thr Asp Val Glu
225                 230                 235                 240

Tyr Glu Ser Asp Glu Lys Ala Arg Gly Thr Arg Leu Asp Gly Leu Asp
                245                 250                 255

Leu Val Asp Thr Trp Lys Ser Phe Lys Pro Arg His Lys His Ser His
            260                 265                 270

Phe Ile Trp Asn Arg Thr Glu Leu Leu Thr Leu Asp Pro His Asn Val
            275                 280                 285

Asp Tyr Leu Leu Gly Leu Phe Glu Pro Gly Asp Met Gln Tyr Glu Leu
            290                 295                 300

Asn Arg Asn Asn Val Thr Asp Pro Ser Leu Ser Glu Met Val Val Val
305                 310                 315                 320

Ala Ile Gln Ile Leu Arg Lys Asn Pro Lys Gly Phe Phe Leu Leu Val
                325                 330                 335

Glu Gly Gly Arg Ile Asp His Gly His His Glu Gly Lys Ala Lys Gln
            340                 345                 350

Ala Leu His Glu Ala Val Glu Met Asp Arg Ala Val Gly Gln Ala Gly
            355                 360                 365

Ser Leu Thr Ser Ser Glu Asp Thr Leu Thr Val Val Thr Ala Asp His
370                 375                 380

Ser His Val Phe Thr Phe Gly Gly Tyr Thr Pro Arg Gly Asn Ser Ile
385                 390                 395                 400

Phe Gly Leu Ala Pro Met Leu Ser Asp Thr Asp Lys Lys Pro Phe Thr
                405                 410                 415

Ala Ile Leu Tyr Gly Asn Gly Pro Gly Tyr Lys Val Val Gly Gly Glu
                420                 425                 430

Arg Glu Asn Val Ser Met Val Asp Tyr Ala His Asn Asn Tyr Gln Ala
            435                 440                 445

Gln Ser Ala Val Pro Leu Arg His Glu Thr His Gly Gly Glu Asp Val
            450                 455                 460

Ala Val Phe Ser Lys Gly Pro Met Ala His Leu Leu His Gly Val His
465                 470                 475                 480

Glu Gln Asn Tyr Val Pro His Val Met Ala Tyr Ala Ala Cys Ile Gly
                485                 490                 495

Ala Asn Leu Gly His Cys Ala Pro Ala Ser Ser Ala Gly Arg Ser
            500                 505                 510

<210> SEQ ID NO 18
<211> LENGTH: 22
```

```
-continued

<212> TYPE: DNA
<213> ORGANISM: Artificial Sequence
<220> FEATURE:
<223> OTHER INFORMATION: Description of Artificial
      Sequence:oligonucleotide

<400> SEQUENCE: 18
agatcttagt aaggatccag at                                             22
```